(12) United States Patent
Couch

(10) Patent No.: US 8,318,984 B2
(45) Date of Patent: Nov. 27, 2012

(54) INDUCING CYATHIN $A_3$ PRODUCTION

(75) Inventor: Robin Couch, Bristow, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 29 days.

(21) Appl. No.: 12/953,695

(22) Filed: Nov. 24, 2010

(65) Prior Publication Data

US 2011/0295040 A1    Dec. 1, 2011

Related U.S. Application Data

(63) Continuation of application No. PCT/US2009/003252, filed on May 28, 2009.

(60) Provisional application No. 61/056,496, filed on May 28, 2008.

(51) Int. Cl.
*C07C 49/737* (2006.01)
*C12P 39/00* (2006.01)

(52) U.S. Cl. .......................................... 568/373; 435/72
(58) Field of Classification Search ................. 568/373; 435/42

See application file for complete search history.

(56) References Cited

OTHER PUBLICATIONS

Cyathin, a new antibiotic complex produced by *Cyathus helenae*, by Allbutt et al., Can. J. Microbiol., 17: 1401-1407, 1971.
The physiology of production of the antibiotic cyathin by *Cyathus helenae*, by Brodie et al., Can. J. Microbiol., 17: 1243-1245, 1971.
Three Students Serve Apprenticeship with Chemistry Professor, by Driver, Mar. 9, 2007, http://gazette.gmu.edu/articles/9863.

*Primary Examiner* — Sikarl Witherspoon
(74) *Attorney, Agent, or Firm* — David Grossman; Edgar Rodriguez

(57) ABSTRACT

This invention provides a method of producing cyathin $A_3$ in a culture of *Cyathus helenae*. It employs added bacteria to stimulate production of cyathin $A_3$.

16 Claims, 1 Drawing Sheet concentration of cyathin A₃ (mg/mL) vs Time of Induction (days)

INDUCING CYATHIN A₃ PRODUCTION

CROSS REFERENCE TO RELATED APPLICATION

This application is a continuation of International Application No. PCT/US2009/003252, filed in US Receiving Office May 28, 2009, which claims benefit of priority to U.S. Provisional Application No. 61/056,496, filed May 28, 2008, which is incorporated by reference in its entirety into this application.

BACKGROUND OF THE INVENTION

Nerve growth factor (NGF) is a neurotrophic factor in mammals whose induction is triggered by various physiological perturbations to the nervous system, including nerve lesions and excitotoxic destruction. As a result of such perturbations, nearby glial and fibroblast cells may increase production of NGF. In turn, NGF promotes neuronal survival by initiating a signal transduction cascade, which begins with the binding of NGF to specific receptors on the surface of neuronal cells.

Therapy employing NGF has been suggested as a method of preventing or reducing the atrophy and loss of neuronal cells that may occur during a stroke or in neurodegenerative disorders, such as amyotrophic lateral sclerosis (ALS), Alzheimer's disease, and Huntington's disease. However, since NGF itself cannot cross the blood-brain barrier, exogenous NGF would have to be administered directly into the brain. Obviously, the need for such a process severely limits the therapeutic potential of exogenous NOF treatment. However, a promising alternative is endogenous NGF treatment; this alternative depends on the possibility of inducing—i.e., stimulating—the production of NGF within the brain. The development of small-molecule inducers of endogenous NGF would allow the full potential of NGF therapy to be exploited. In experiments with astrocytoma cells, cyathin $A_3$ and the structurally similar products erinacine C and scabronine A have demonstrated significant NGF-inducing activity. Elucidating the mechanism by which these compounds induce NGF is expected to aid significantly in the future development endogenous NGF therapy.

In the 1970s, H. J. Brodie and coworkers reported production of cyathin $A_3$ by *Cyathus helenae* strain 1500. In Brodie's most preferred method, yields of approximately 130 μg/mL cyathin $A_3$ were reported as resulting from the use of static liquid cultures with 30 mL media (30 g/L glucose, 1.5 g/L asparagine, 1 g/L $KH_2PO_4$, 0.5 g/L $Ca(NO_3)_2.4H_2O$, 0.5 g/L $MgSO_4.7H_2O$, 0.25 mg/L $ZnSO_4.2H_2O$, and 0.15 mg/L thiamine) in a 125 mL flask, inoculated with a 8 mm diameter agar plug of fungal mycelium (obtained from the edges of a 5 day old culture), and incubated at room temperature for 30 days. However, this method has been plagued by low yields and poor reproducibility.

SUMMARY OF THE INVENTION

In one embodiment, this invention provides a method for producing cyathin $A_3$ comprising the following steps: initiating a culture by inoculating a medium with a *Cyathus* strain isolated from one or more nutrient sources; incubating the culture for a first incubation period, with optional shaking; introducing a bacterium to the culture; further incubating the culture for a second incubation period, with optional shaking; removing the *Cyathus* from the mixture; and isolating the cyathin $A_3$ from the mixture by extraction with an organic solvent. Any convenient size of incubation flasks may be used.

In another embodiment, the first incubation period lasts from about 1 day to about 40 days, and the second incubation period lasts from about 12 hours to about 12 days.

In another embodiment, the bacterium is *E. coli*.

In another embodiment, the incubation temperature is maintained constant at from about 5° C. to about 45° C.

In another embodiment, the incubation takes place in 125 mL flasks, each containing 50 mL of media.

In another embodiment, the first incubation period is from about 10 days to about 30 days, and the second incubation period is from about 3 days to about 9 days.

BRIEF DESCRIPTION OF THE DRAWINGS

FIG. 1 presents data demonstrating that timing of introduction of *E. coli* into a *Cyathus* culture has an effect on cyathin $A_3$ production.

DETAILED DESCRIPTION OF THE INVENTION

The present invention provides reliable methods for producing cyathin $A_3$ in cell culture. As noted below, as methods provide a significant increase in yield over that reported for the Brodie method. The increase in yield over that reported for the Brodie method can be 7-fold or more.

This invention provides a method of producing cyathin $A_3$ in cell culture through the use of added bacteria to induce production of cyathin $A_3$. The bacteria may be added 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days after initiation of the cell culture. Any strain of *Cyathus helenae* may be used, and any strain of *E. coli* may be added to the cell culture. Incubation may occur at temperatures from 5° C. to 45 C. The previously described Brodie media may be used for the cell culture, or any other media appropriate for culturing *Cyathus* may be used. Various sizes of flasks, volumes of media or other culture conditions may be employed, as desired, and the culture may be grown with or without the aid of shaking. Cyathin $A_3$ production can be initiated with any gram negative or positive bacteria, as well as fungi including but not limited to *Pseudomonas, Bacillus, Penicillium, Aspergillus, Saccharomyces* among others. Isolation of the product may be by gravity filtration followed by extraction of the culture media with an organic solvent although other purification methods may be used. Gravity filtration may optionally employ Celite® or other filter aid. The extraction may utilize a variety of organic solvents, including ethyl acetate. The extraction procedure may optionally be facilitated through the use of pH adjustment of the aqueous phase via addition of concentration HCl or other acid solution. The extraction procedure may also optionally be facilitated through the use of ionic strength adjustment of the aqueous phase, via addition of NaCl.

EXAMPLE 1

Brodie-agar plates were produced by pouring into petri plates solutions of the following composition: 2 g/L glucose, 5 g/L maltose, 0.8 mL glycerol, 0.2 g/L peptone, 0.2 g/L L-asparagine, 2 g/L yeast extract, 0.5 g/L $KH_2PO_4$, 0.5 g/L $Ca(NO_3)_2.4H_2O$, 0.5 g/L $MgSO_4.7H_2O$, 2 mg/L $FeSO_4$, and 20 g/L agar. These plates were inoculated with *Cyathus helenae* mycelium obtained from American Type Culture Collection (ATCC), Manassas, Va. Once the fungus had reached an appropriate diameter, sugar-cube-sized cubes were cut out of the agar with a sterilized instrument. These agar plugs containing *Cyathus helenae* mycelium were used to inoculate 125 mL flasks containing 50 mL of "Brodie Media" (identical to the culture media except for the agar).

The cultures were incubated at 28° C. without shaking. After the cultures had been initiated, a 1 mL aliquot of *E. coli* culture (obtained from an overnight liquid culture grown in Luria Bertani (LB) media) was introduced into the flasks at 11, 12, 13, 14, 15, 19, 20, 22, 25, 26 and longer after culture initiation. After about 6 additional days of incubation, the *Cyathus helenae* mycelium was removed by vacuum filtration, and, in a separatory funnel, the filtrate was extracted 3 times with equal volumes of ethyl acetate. The combined extracts were dried over anhydrous magnesium sulfate, then concentrated by rotary evaporation. The extract was stored at 4° C. prior to HPLC analysis.

Fractions from the media extract have a UV absorption spectrum identical to that of authentic cyathin $A_3$. Additonally, LC-MS analysis (using a Waters EMD1000 LC-MS in electrospray ionization (ESI) negative mode; [M-H]=317.4) confirms that this peak is cyathin $A_3$. The concentration of cyathin in the medium was determined by HPLC analysis.

As shown in FIG. 1, the 50 ml culture produced about 1.3, 1.6, 2.8, 2.9 and 3.7 mg/ml cyathin $A_3$ when *E. coli* was added 11, 12, 13, 14 and 15 days after culture initiation respectively. No cyathin $A_3$ was produced in 50 ml cultures that were not exposed to *E. coli*. These results demonstrate a significant improvement over the 130 µg/mL reported by Brodie of cyathin products in *C. helenae* cultures. The method is reproducible and provides a significantly better yield than the earlier published method.

The foregoing descriptions of examples and embodiments of the claimed invention have been presented for purposes of illustration and description. They are not intended to be exhaustive or be limiting to the precise forms disclosed; as the skilled artisan will immediately recognize, many modifications and variations are possible in light of the above teaching. The illustrated embodiments were chosen and described in order to best explain the principles of the claimed invention and its practical application. Thus, the claimed invention should not be limited by any of the examples or embodiments described above.

What is claimed is:

1. A method for producing cyathin A3 comprising:
   a. initiating a culture by inoculating a medium with a *Cyathus* strain isolated from one or more nutrient sources;
   b. initially incubating said culture for a first incubation period, optionally with shaking;
   c. introducing a bacterium to the culture;
   d. further incubating the culture for a second incubation period, optionally with shaking;
   e. removing the *Cyathus* from the mixture; and
   f. isolating the cyathin A3 from the mixture by extraction with an organic solvent.

2. The method of claim 1, wherein the first incubation period last from about 1 day to about 40 days, wherein the second incubation period lasts from about 12 hours to about 12 days, and wherein the bacterium is *E. coli*.

3. The method of claim 2, wherein the incubation temperature is maintained constant at from about 5 degrees C. to about 45 degrees C.

4. The method of claim 3, wherein the incubation temperature is maintained constant at from about 10 degrees C. to about 40C.

5. The method of claim 4, wherein the incubation time is maintained constant at from about 15 degrees C. to about 35 degrees C.

6. The method of claim 5, wherein the incubation temperature is maintained constant at from about 20 degrees C. to about 30 degrees C.

7. The method of claim 1, wherein the incubation takes place in 125 mL flasks, each containing 50 mL of media.

8. The method of claim 1, wherein the first incubation period is from about 10 days to about 30 days, and wherein the second incubation period is from about 3 to about 9 days.

9. The method of claim 1, wherein the first incubation period is from about 25 days to about 30 days, and wherein the second incubation period is from about 5 days to about 7 days.

10. The method of claim 9, wherein the *Cyathus* strain is *Cyathus helenae*.

11. The method of claim 1, wherein the bacterium is *E. coli*.

12. A method of producing cyathin A3 comprising:
   a. initiating a culture by inoculating a medium with a *Cyathus* strain;
   b. incubating said culture for a first incubation period;
   c. introducing a bacterium to the culture; and
   d. incubating the culture for a second incubation period.

13. The method of claim 12, further comprising isolating the cyathin A3.

14. A composition comprising:
   a. a *Cyathus* strain;
   b. a bacterium; and
   c. cyathin A3.

15. The composition of claim 14, wherein the *Cyathus* strain is *Cyathus helenae*.

16. The composition of claim 14, wherein the bacterium is *E. coli*.

* * * * *